(12) United States Patent
Yi et al.

(10) Patent No.: US 11,938,274 B2
(45) Date of Patent: Mar. 26, 2024

(54) ELECTRONIC ATOMIZING DEVICE AND VENTILATION VALVE THEREOF

(71) Applicant: SHENZHEN SMOORE TECHNOLOGY LIMITED, Shenzhen (CN)

(72) Inventors: Changyong Yi, Shenzhen (CN); Zhenlong Jiang, Shenzhen (CN); Congwen Xiao, Shenzhen (CN); Xiaoping Li, Shenzhen (CN); Lingrong Xiao, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 918 days.

(21) Appl. No.: 16/929,322

(22) Filed: Jul. 15, 2020

(65) Prior Publication Data
US 2021/0016049 A1    Jan. 21, 2021

(30) Foreign Application Priority Data

Jul. 16, 2019    (CN) .......................... 201910642518.8

(51) Int. Cl.
*A61M 11/00*    (2006.01)
*A61M 11/04*    (2006.01)
*A61M 16/20*    (2006.01)

(52) U.S. Cl.
CPC ........ *A61M 16/206* (2014.02); *A61M 11/042* (2014.02); *A61M 2205/02* (2013.01)

(58) Field of Classification Search
CPC .............. A61M 16/206; A61M 11/042; A61M 2205/02; A61M 11/00; A61M 15/0001;
(Continued)

(56) References Cited

U.S. PATENT DOCUMENTS 5,113,855 A *   5/1992   Newhouse ........ A61M 15/0093
                                                          128/203.15
9,827,384 B2 *  11/2017  Holakovsky ...... A61M 15/0036
(Continued)

FOREIGN PATENT DOCUMENTS

CN     205813569 U    12/2016
CN     107249363 A    10/2017
(Continued)

OTHER PUBLICATIONS

Machine translation of claims and written description from espacenet for WO2012106739 (Year: 2012).*
(Continued)

*Primary Examiner* — Michael R Reid
*Assistant Examiner* — Tyler A Raubenstraw
(74) *Attorney, Agent, or Firm* — Dorsey & Whitney LLP

(57) ABSTRACT

The present disclosure relates to a ventilation valve configured to be mounted to a liquid reservoir of an electronic atomizing device. The ventilation valve includes: a valve sleeve connected to the liquid reservoir and provided with a through hole, the through hole in communication with a storage cavity of the liquid reservoir; and a valve element having air permeability and including an oleophobic material layer adjacent to the storage cavity, and a semi-permeable membrane connected to an end of the oleophobic material layer away from the storage cavity, the oleophobic material layer filling at least a part of the through hole.

19 Claims, 7 Drawing Sheets

(58) Field of Classification Search
CPC ....... A61M 15/00; A61M 15/06; A24F 40/00; A24F 1/00–2700/08
See application file for complete search history.

(56) References Cited

U.S. PATENT DOCUMENTS

| | | | |
|---|---|---|---|
| 10,188,146 B2* | 1/2019 | Chen | H05B 3/46 |
| 10,306,920 B1* | 6/2019 | Valdes | F23Q 7/16 |
| 10,349,678 B2* | 7/2019 | Chen | H05B 1/0227 |
| 10,588,176 B2* | 3/2020 | Marsh | A24F 40/46 |
| 10,624,391 B2* | 4/2020 | Chen | A61M 15/0021 |
| 10,765,151 B2* | 9/2020 | Rostami | A24F 40/10 |
| 10,821,240 B2* | 11/2020 | McCullough | H05B 1/025 |
| 11,571,529 B2* | 2/2023 | Woias | A61M 15/06 |
| 2003/0140923 A1* | 7/2003 | Taylor | A61M 15/0055 128/203.15 |
| 2004/0025865 A1* | 2/2004 | Nichols | A61M 15/0066 128/200.14 |
| 2006/0086738 A1 | 4/2006 | Dehn et al. | |
| 2009/0223515 A1* | 9/2009 | Watanabe | A61M 15/0036 128/203.15 |
| 2010/0269819 A1* | 10/2010 | Sievers | A61M 15/00 128/200.23 |
| 2011/0126837 A1* | 6/2011 | Winter | A61M 16/206 128/205.12 |
| 2012/0247463 A1* | 10/2012 | Zoltan | A61M 15/0025 128/203.15 |
| 2014/0096781 A1* | 4/2014 | Sears | A24F 40/00 131/328 |
| 2014/0261486 A1* | 9/2014 | Potter | A24F 40/30 131/328 |
| 2015/0201674 A1* | 7/2015 | Dooly | A24F 40/42 131/328 |
| 2017/0045150 A1 | 2/2017 | Marsh | |
| 2017/0086496 A1* | 3/2017 | Cameron | B25F 1/04 |
| 2017/0099878 A1* | 4/2017 | Murison | A24F 15/015 |
| 2017/0182267 A1* | 6/2017 | Cameron | A61M 11/042 |
| 2017/0224937 A1* | 8/2017 | Schuschnig | A61M 11/003 |
| 2017/0231274 A1* | 8/2017 | Davis | B65B 3/14 |
| 2017/0341850 A1* | 11/2017 | Sebastian | A24F 40/30 |
| 2017/0368273 A1* | 12/2017 | Rubin | A61M 16/0093 |
| 2018/0015240 A1* | 1/2018 | Zheng | A61M 15/0028 |
| 2018/0020730 A1* | 1/2018 | Alarcon | A24F 40/42 131/329 |
| 2018/0056015 A1* | 3/2018 | Shwadchuck | A61M 15/0021 |
| 2018/0070634 A1* | 3/2018 | Sur | A61M 11/042 |
| 2018/0263283 A1* | 9/2018 | Popplewell | A24B 15/167 |
| 2018/0289065 A1* | 10/2018 | Liao | A24F 7/04 |
| 2018/0360110 A1* | 12/2018 | Marsot | A61M 15/0013 |
| 2019/0001096 A1* | 1/2019 | Pratt, Jr. | A61M 11/042 |
| 2019/0166907 A1* | 6/2019 | Chung | A24F 40/485 |
| 2019/0191769 A1* | 6/2019 | Qiu | A24F 40/485 |
| 2019/0247606 A1* | 8/2019 | Williams | A24F 40/485 |
| 2020/0121868 A1* | 4/2020 | Reshef | A61M 15/0021 |
| 2020/0170295 A1* | 6/2020 | Grimm | A24F 13/00 |
| 2020/0367553 A1* | 11/2020 | Hejazi | A24F 40/48 |
| 2021/0145063 A1* | 5/2021 | Perrins | A24F 40/46 |
| 2022/0257880 A1* | 8/2022 | Petrikova | A61M 15/0086 |

FOREIGN PATENT DOCUMENTS

| | | | | |
|---|---|---|---|---|
| CN | 208192139 U | | 12/2018 | |
| CN | 208597718 U | | 3/2019 | |
| CN | 208740121 U | | 4/2019 | |
| CN | 109770437 A | | 5/2019 | |
| CN | 109805459 A | | 5/2019 | |
| CN | 209498557 U | * | 10/2019 | |
| CN | 210960420 U | | 7/2020 | |
| DE | 202011104284.0 U1 | | 11/2011 | |
| DE | 102017123869 A1 | | 4/2019 | |
| EP | 3692837 A1 | * | 8/2020 | ............ A24F 40/30 |
| EP | 3692844 A1 | * | 8/2020 | ............ A24F 40/30 |
| EP | 3711798 A1 | * | 9/2020 | ............ A24F 40/42 |
| GB | 2492155 A | * | 12/2012 | ............ A61L 9/037 |
| GB | 2542007 A | | 3/2017 | |
| GB | 2542013 A | * | 3/2017 | ........... A24F 47/002 |
| WO | WO-0100263 A2 | * | 1/2001 | ........... A61M 15/002 |
| WO | WO-2012026963 A2 | * | 3/2012 | ........... A61M 11/005 |
| WO | WO-2012106739 A1 | * | 8/2012 | ............ A24F 40/42 |
| WO | WO-2013067592 A1 | * | 5/2013 | ........ A61M 16/0003 |
| WO | WO-2013076696 A1 | * | 5/2013 | ............ A24F 47/002 |
| WO | WO-2016203228 A1 | * | 12/2016 | ........... A61M 11/007 |
| WO | WO-2018045418 A1 | * | 3/2018 | ............ A61M 11/04 |
| WO | WO-2018107539 A1 | * | 6/2018 | ............ A61M 11/00 |
| WO | WO-2018193456 A1 | * | 10/2018 | ........... A61M 15/002 |
| WO | WO-2019173923 A1 | * | 9/2019 | ............ A24F 40/42 |
| WO | WO-2020034774 A1 | * | 2/2020 | ............ A24F 40/10 |
| WO | WO-2020124260 A1 | * | 6/2020 | ............ A24F 40/30 |
| WO | WO-2020255044 A1 | * | 12/2020 | ........... A24F 40/485 |

OTHER PUBLICATIONS

Machine translation of claims and written description from espacenet for CN209498557 (Year: 2018).*
Communication Pursuant to Article 94(3) EPC for European Patent Application No. 20186166.3 dated Jan. 30, 2023.
Extended European Search Report for European Application No. 20186166.3 dated Nov. 16, 2020.
First Office Action for Chinese Application No. 201910642518.8 dated Nov. 24, 2023.

* cited by examiner

ELECTRONIC ATOMIZING DEVICE AND VENTILATION VALVE THEREOF

CROSS-REFERENCE TO RELATED APPLICATION

This application claims priority to Chinese Patent Application No. 2019/106425188, filed on Jul. 16, 2019, the entire content of which is incorporated herein by reference.

TECHNICAL FIELD

The present disclosure relates to a field of electronic atomizing technology, in particular, to a ventilation valve and an electronic atomizing device including the same.

BACKGROUND

In a process of suction and atomization of an electronic atomizing device, a continuous consumption of liquid will gradually accumulate a certain negative pressure in a liquid reservoir that stores the liquid. As the negative pressure continues to increase, the liquid will be difficult to be transported to an atomizing surface of a porous heating element for atomization, subjected to a capillary effect. Due to insufficient liquid supply, the electronic atomizing device generates scorching smell and other harmful substances, which in turn affects user's inhaling experience.

SUMMARY

According to various embodiments, a ventilation valve and an electronic atomizing device including the same are provided.

A ventilation valve configured to be mounted to a liquid reservoir of an electronic atomizing device includes: a valve sleeve connected to the liquid reservoir and provided with a through hole, the through hole in communication with a storage cavity of the liquid reservoir; and a valve element having air permeability and including an oleophobic material layer and adjacent to the storage cavity, and a semi-permeable membrane connected to an end of the oleophobic material layer away from the storage cavity, the oleophobic material layer filling at least a part of the through hole.

A ventilation valve includes a valve sleeve; and a valve element having air permeability and comprising an oleophobic material layer, and a semi-permeable membrane connected to an end of the oleophobic material layer.

An electronic atomizing device includes a liquid reservoir having a storage cavity and the ventilation valve as described above. The liquid reservoir is provided with a mounting hole communicating with the storage cavity. The ventilation valve is received in the mounting hole.

Since the oleophobic material layer can fill at least a part of the through hole, the liquid in the storage cavity cannot leak out through the through hole and the valve element, the storage cavity can be effectively prevented from liquid leakage. Moreover, when the liquid in the storage cavity is gradually consumed because of the atomization, the air can enter the storage cavity through the valve element to fill a space released by the liquid in time, such that air pressure in the storage cavity is kept within a normal range. Due to the air pressure, the liquid in the storage cavity can be smoothly supplied to the atomizing core of the electronic atomizing device for atomization, to ensure that the atomizing core can always obtain enough liquid during the atomizing process, so as to avoid scorching caused by the insufficient liquid supply.

DETAILED DESCRIPTION OF THE EMBODIMENTS

For the convenience of understanding of the present disclosure, the present disclosure will be described more fully with reference to related drawings. However, the present disclosure can be implemented in many different forms and is not limited to the embodiments described herein. In contrast, providing these embodiments is to providing a fully and thoroughly understanding of the disclosure of the present disclosure.

It should be noted that when an element is referred as to be "fixed" to another element, it can be directly on another element or there may be an intermediate element therebetween. When an element is considered to be "connected" to another element, it may be directly connected to another element or there may be an intermediate element therebetween at the same time. The terms "inner", "outer", "left", "right" and the like used herein are for illustration only and are not meant to be the only embodiment.

Figure 1:
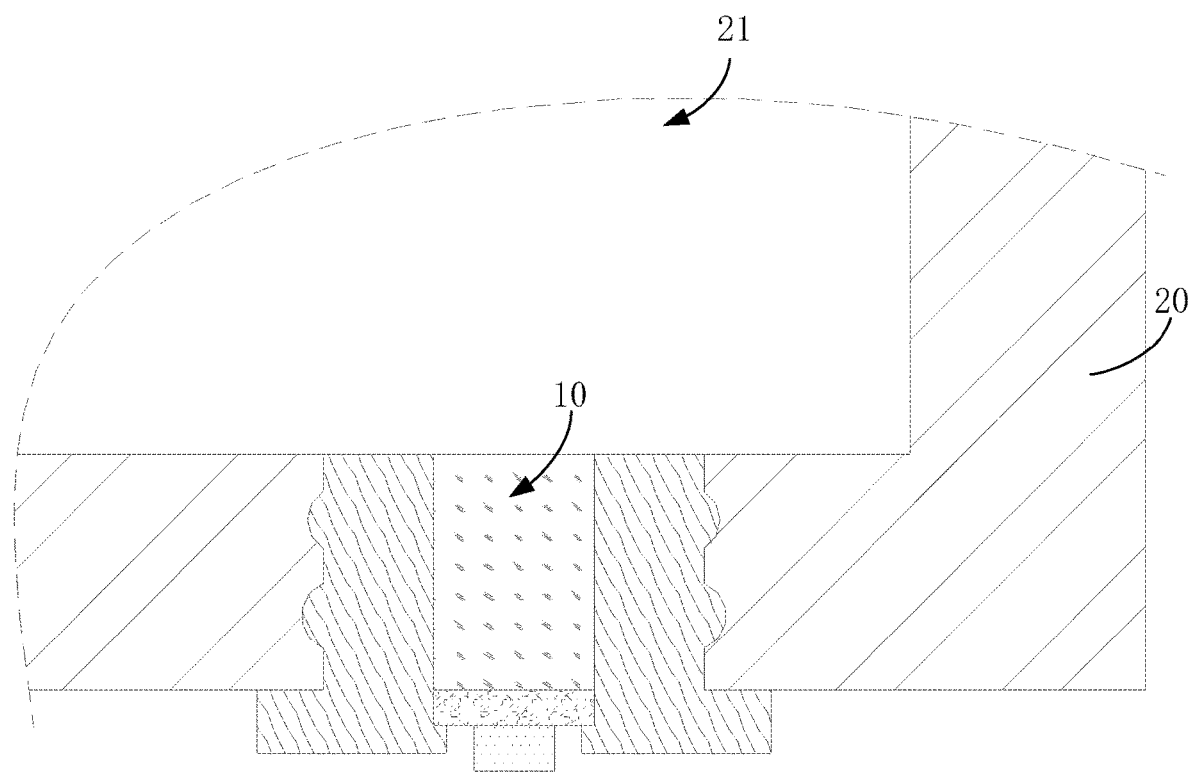
FIG. 1 is a partial cross-sectional view of an electronic atomizing device according to an embodiment.

Referring to FIG. 1, an electronic atomizing device according to an embodiment includes a ventilation valve 10 and a liquid reservoir 20. The liquid reservoir 20 is provided with a storage cavity 21 therein. The storage cavity 21 is used to store liquid, which is capable of generating an aerosol gel. The storage cavity 21 can supply liquid to an atomizing core (not shown) of the electronic atomizing device. The atomizing core may have a porous ceramic structure. Subjected to a capillary effect, the atomizing core absorbs the liquid in the storage cavity 21 and atomize it to aerosol gel for the user to inhale.

Figure 2:
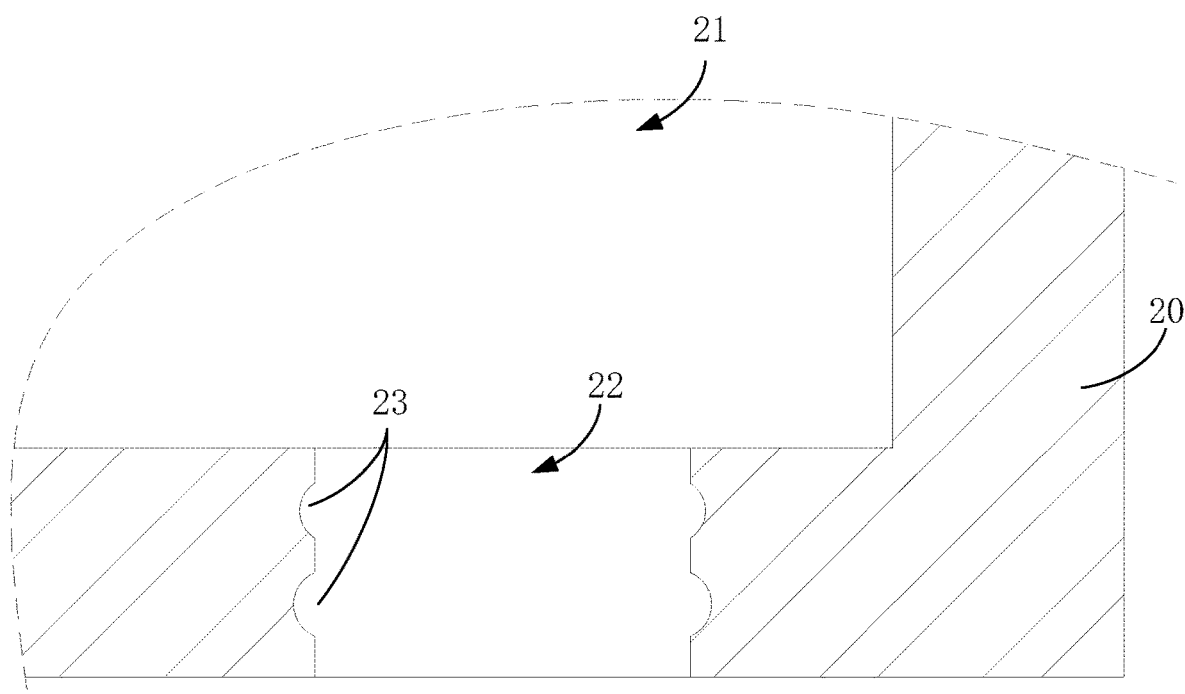
FIG. 2 is an enlarged view of a liquid reservoir in FIG. 1.

Referring to FIG. 2, in some embodiments, the liquid reservoir 20 is provided with a mounting hole 22 at a bottom portion thereof. The mounting hole 22 is a through hole and communicates with the storage cavity 21. A plurality of circular grooves 23 are formed on a sidewall of the mounting hole 22. The plurality of circular grooves 23 are spaced apart with an interval in an axial direction of the mounting hole 22.

Figure 3:
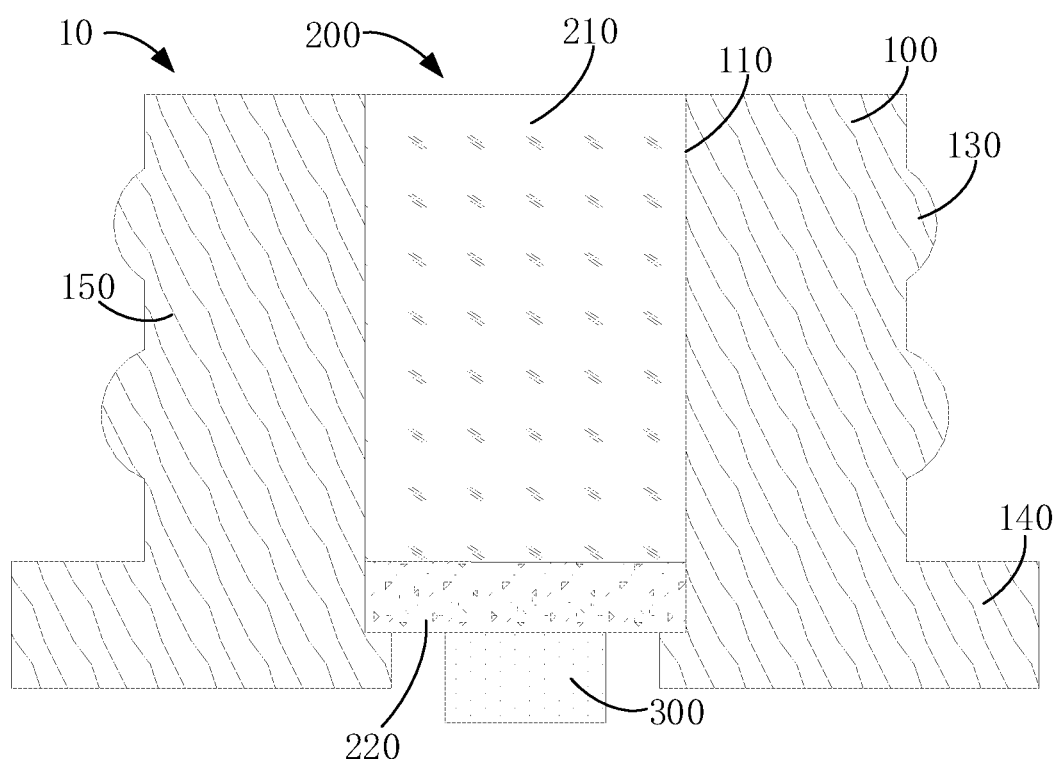
FIG. 3 is an enlarged view of a ventilation valve in FIG. 1.

Referring to FIG. 3, the ventilation valve 10 includes a valve sleeve 100 and a valve element 200. The valve sleeve 100 is provided with a through hole 110. When the valve sleeve 100 is received in the mounting hole 22 of the liquid reservoir 20, the through hole 110 is in fluid communication with the storage cavity 21 of the liquid reservoir 20.

The valve sleeve 100 may be made of silicone, which has a good sealing effect. The valve sleeve 100 includes a main body 150 and a flange portion 140. The main body 150 is fixed in the mounting hole 22, and the flange portion 140 is provided at an end of the main body 150 away from the storage cavity 21. A plurality of protruding rings 130 corresponding to the circular grooves 23 are provided on an out surface of the main body 150. The plurality of protruding rings 130 are spaced apart with an interval in the axial direction of the valve sleeve 100. The plurality of protruding rings 130 can be embedded in the plurality of circular grooves 23 of the liquid reservoir 20. For example, when the main body 150 is received in mounting hole 22, each protruding ring 130 is embedded in a corresponding circular groove 23. As such, the connection strength between the valve sleeve 100 and the liquid reservoir 20 can be enhanced, while the sealing property of the main body 150 and the protruding ring 130 with respect to the mounting hole 22 can be ensured, thereby preventing the liquid from leaking out from the mounting hole 22. The flange portion 140 may extend in a direction perpendicular to the axial direction of the main body 150. When the main body 150 is mounted in the mounting hole 22, the flange portion 140 can abut against a bottom surface of the liquid reservoir 20. In fact, the flange portion 140 has a position limiting effect on the entire valve sleeve 100 when it is mounted, thereby improving the mounting accuracy of the valve sleeve 100.

Figure 6:
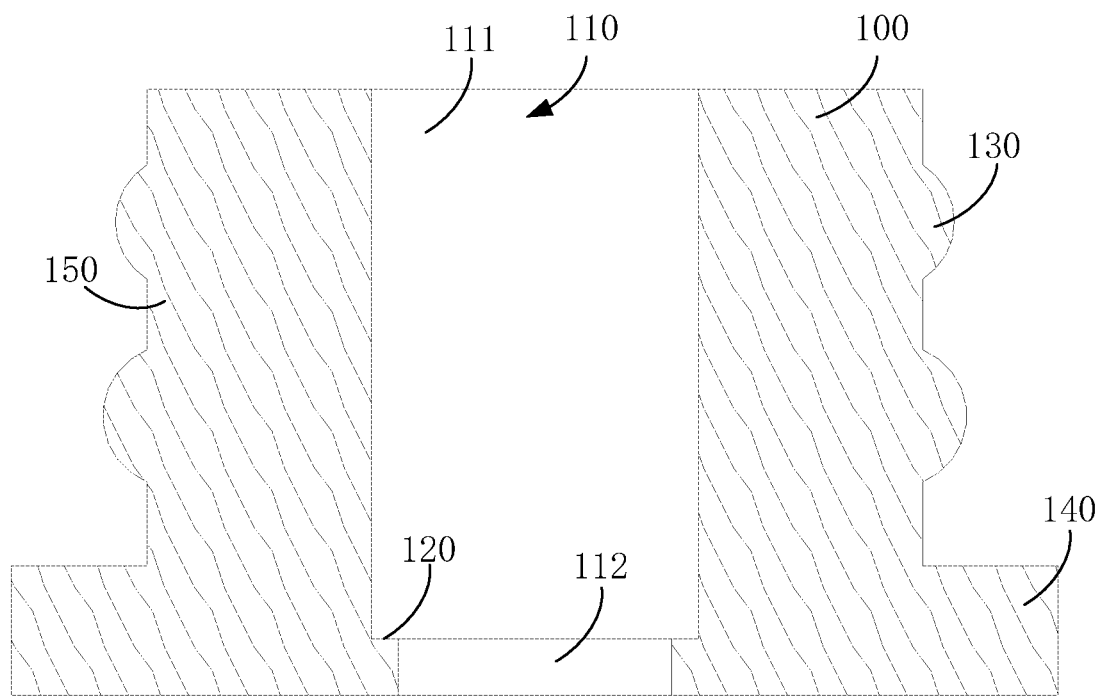
FIG. 6 is a cross-sectional view of a valve sleeve in FIG. 3.

Referring to FIGS. 3 and 6, a stepped portion 120 is formed on a portion of an inner surface of the through hole 110. Accordingly, the through hole 110 is composed of a first hole 111 and a second hole 112 that are arranged coaxially. A diameter of the first hole 111 is greater than a diameter of the second hole 112, and a bottom wall of the first hole 111 constitutes the stepped portion 120. An end of the valve element 200 may abut against the stepped portion 120, such that the stepped portion 120 has a good positioning effect on the valve element 200 and improves the mounting accuracy of the valve element 200 when mounting the valve element 200. Moreover, the valve element 200 is prevented from loosening and escaping from the through hole 110.

The valve element 200 is used to block the through hole 110. The valve element 200 has both of good liquid isolation property and air permeability. In other words, the valve element 200 can prevent the liquid from leaking while allowing air to pass through. Due to the valve element 200, the liquid in the storage cavity 21 cannot leak out through a gap between the valve element 200 and the valve sleeve 100, and the liquid cannot leak out from a surface of the valve element 200 by infiltrating into the valve element 200. Therefore, the valve element 200 can, on one hand, prevent the storage cavity 21 from liquid leakage, on the other hand and more importantly, when the liquid in the storage cavity 21 is gradually consumed, the air can enter the storage cavity 21 through the valve element 200 to fill the space released by the liquid in time, such that air pressure in the storage cavity 21 is kept within a normal range. Due to the normal air pressure, the liquid in the storage cavity 21 can be smoothly supplied to the atomizing core, such that the atomizing core can always obtain enough liquid during the atomizing process, so as to avoid scorching caused by the insufficient liquid supply.

Referring to FIG. 3, the valve element 200 includes an oleophobic material layer 210 and a semi-permeable membrane 220 connected to an end of the oleophobic material layer 210. The oleophobic material layer 210 fills at least a part of the through hole 110. Specifically, when a thickness of the oleophobic material layer 210 in an axial direction of the through hole 110 is less than a length of the through hole 110, the oleophobic material layer 210 fills a part of the through hole 110; when the thickness of the oleophobic material layer 210 in the axial direction of the through hole 110 is equal to the length of the through hole 110, the oleophobic material layer 210 can fill the entire through hole 110.

Figure 4:
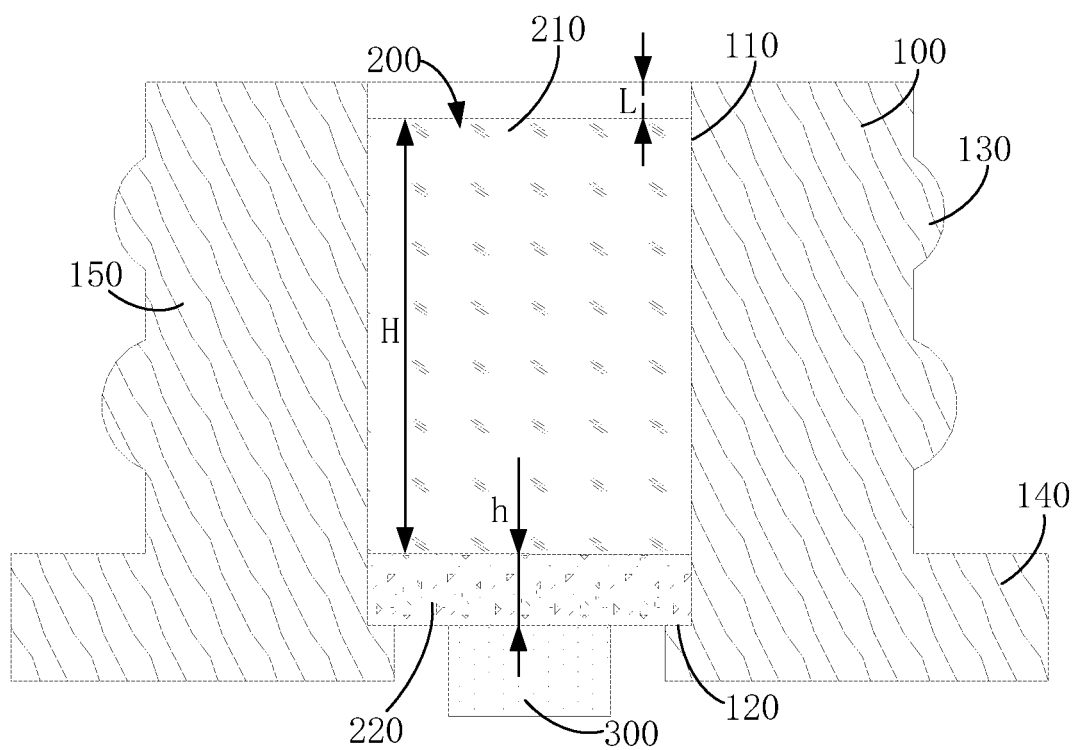
FIG. 4 is a cross-sectional view of a ventilation valve according to another embodiment.

Referring to FIG. 4, in one embodiment, the thickness of the oleophobic material layer 210 is less than the length of the through hole 110, such that an end of the valve element 200 adjacent to the storage cavity 21 may be lower than a top portion of the valve sleeve 100 by a preset height difference L. A space defined by the preset height distance L can effectively increase an air storage space of the storage cavity 21, such that the air pressure in the storage cavity 21 can be kept within a normal range. In other embodiments, referring to FIG. 3, a top surface of the oleophobic material layer 210 may also be coplanar with the end of the valve sleeve 100.

In some embodiments, the oleophobic material layer 210 may be made of a rigid material, that is, the oleophobic material layer 210 has a certain deformation resistance, thereby enhancing the structural strength of the entire ventilation valve 10. The oleophobic material layer 210 may also form an interference fit with the through hole 110, such that the oleophobic material layer 210 is always in a firm contact with an inner surface of the through hole 110, so as to ensure that a good sealing effect is formed between the oleophobic material layer 210 and the through hole 110.

In some embodiments, the oleophobic material layer 210 may be made of an organic material, such as polyvinylidene fluoride, polytetrafluoroethylene, polypropylene, polyamide, and polypropylene. The oleophobic material layer 210 may also be made of inorganic material, such as alumina after hydrophobic treatment, diatomaceous earth, silica or the like. The oleophobic material layer 210 may also be made of a composite of both organic material and inorganic material. When the oleophobic material layer 210 is made of the aforementioned material, it can exhibit good oleophobicity (i.e., tending to repel oil). When the oleophobic material layer 210 is in direct contact with the liquid in the storage cavity 21, the liquid cannot infiltrate into the oleophobic material layer 210 and leaks out from a surface of the oleophobic material layer 210, thereby preventing the liquid from leaking out from the storage cavity 21. Meanwhile, there are a large number of air-permeable micropores in the oleophobic material layer 210, such that the oleophobic material layer 210 has good air permeability, and air can enter the storage cavity 21 through the oleophobic material layer 210, such that air pressure in the storage cavity 21 is always kept within the normal range, thus ensuring that the liquid in the storage cavity 21 can be smoothly supplied to the atomizing core. In some embodiments, diameters of the air-permeable micropores may range from 0.05 μm to 20 μm. For example, the diameter of the air-permeable micropores may be 0.05 μm, 0.1 μm, 10 μm, 20 μm or the like.

Referring to FIGS. 3 and 4, the semi-permeable membrane 220 is provided on an end of the oleophobic material layer 210 away from the storage cavity 21. For example, the semi-permeable membrane 220 and the oleophobic material layer 210 are laminated, or the semi-permeable membrane 220 may be embedded in the oleophobic material layer 210. The semi-permeable membrane 220 may be made of materials such as polytetrafluoroethylene and polyvinylidene fluoride, such that the semi-permeable membrane 220 also has good oleophobicity. Therefore, the liquid cannot infiltrate into the semi-permeable membrane 220 and leaks out from a surface of the semi-permeable membrane 220, so as to prevent the liquid from leaking out from the storage cavity 21. Due to the semi-permeable membrane 220, another barrier for preventing the liquid leakage is provided, which can further improve the liquid isolation property of the entire valve element 200. In addition, the oleophobicity of the semi-permeable membrane 220 may be greater than that of the oleophobic material layer 210, so as to further ensure the liquid isolation property of the entire valve element 200. Moreover, the semi-permeable membrane 220 may also has air-permeable micropores. The average diameter of the air-permeable micropores may be less than the average diameter of the air-permeable micropores in the oleophobic material layer 210. For example, the average diameter of the air-permeable micropores in the semi-permeable membrane 220 may range from 0.1 µm to 10 µm, such as 0.1 µm, 0.2 µm, 0.5 µm, 10 µm or the like, such that the semi-permeable membrane 220 has good air permeability. Therefore, the air can enter the storage cavity 21 by passing through the semi-permeable membrane 220 and the oleophobic material layer 210 in sequence, such that air pressure in the storage cavity 21 is always kept within a normal range, so as to ensure that the liquid in the storage cavity 21 can be smoothly supplied to the atomizing core.

Referring to FIG. 4, in the axial direction of the through hole 110, the thickness H of the oleophobic material layer 210 may range from about 0.5 mm to about 2 mm, for example, may specifically be 0.5 mm, 0.9 mm, 1 mm, 2 mm or the like. The thickness h of the semi-permeable membrane 220 may range from about 10 µm to about 50 µm, for example, may specifically be 10 µm, 11 µm, 14 µm, 15 µm or the like. Since the thickness H of the oleophobic material layer 210 is greater than the thickness h of the semi-permeable membrane 220, the thickness of the semi-permeable membrane 220 can be kept within the normal range on the basis of ensuring liquid isolation property and air permeability, such that the semi-permeable membrane 220 will not occupy too much mounting space, so as to ensure a more compact structure of the valve element 200 and even the entire ventilation valve 10. The semi-permeable membrane 220 can be entirely accommodated in the through hole 110, which makes full use of the existing space of the through hole 110, and can also ensure that the compactness of the valve element 200 and the ventilation valve 10. In some embodiments, the oleophobic material layer 210 may also be entirely accommodated in the through hole 110. By accommodating both of the semi-permeable membrane 220 and the oleophobic material layer 210 entirely in the through hole 110, both of them can be well protected by the valve sleeve 100.

Figure 5:
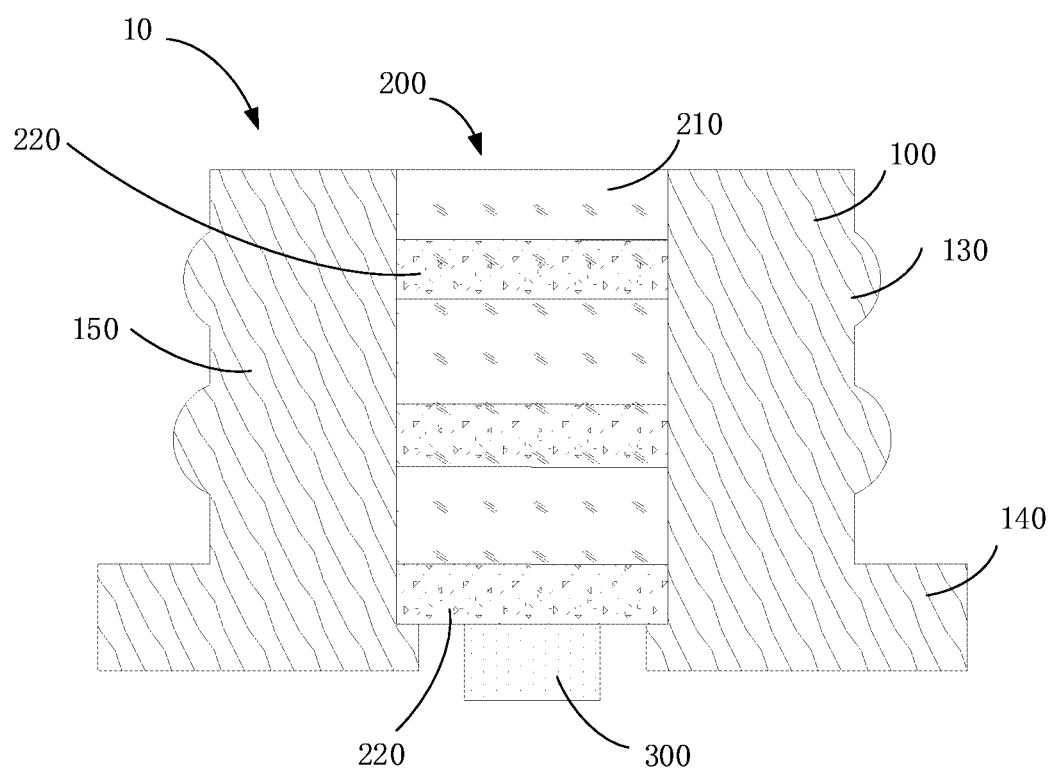
FIG. 5 is a cross-sectional view of a ventilation valve according to yet another embodiment.

In an alternative embodiment, the valve element 100 may include a plurality of oleophobic material layers 210 and a plurality of semi-permeable membranes 220 that are alternately arranged in the axial direction of the through hole 110. Referring to FIG. 5, in the illustrated embodiment, three semi-permeable membranes 220 and three oleophobic material layers 210 are provided, which are alternately laminated on one another in the axial direction of the through hole 110. The semi-permeable membranes 220 on the topmost is in contact with the liquid in the storage cavity 21, and the semi-permeable membranes 220 on the lowermost is in contact with a dust filter 300. Through alternately arranging the oleophobic material layers 210 and the semi-permeable membranes 220 in sequence, the liquid isolation property and air permeability throughout the valve element 200 can be enhanced.

Referring to FIG. 3 and FIG. 4 again, in some embodiments, the ventilation valve 10 further includes a dust filter 300 connected to the valve element 200. The dust filter 300 is partially accommodated in the through hole 110. The dust filter 300 has good air permeability due to its large pore diameter, and air can pass through the dust filter 300 and enter the storage cavity 21 via the valve element 200. The dust filter 300 is located at the end surface of the valve element 200 away from the storage cavity 21. For example, the dust filter 300 is connected to the end surface of the semi-permeable membrane 220 away from the storage cavity 21. The dust filter 300 can prevent large particles of dust and impurities from entering the valve element 200, so as to prevent the dust and impurities from weakening the air permeability of the valve element 200. The dust filter 300 may be made of polymer material or metal material. In one embodiment, the dust filter 300 may be integrally formed with the semi-permeable membrane 220. In other embodiments, the dust filter 300 may be integrally formed with the valve sleeve 100. In that case, the dust filter 300 may be made of silicone.

Figure 7:
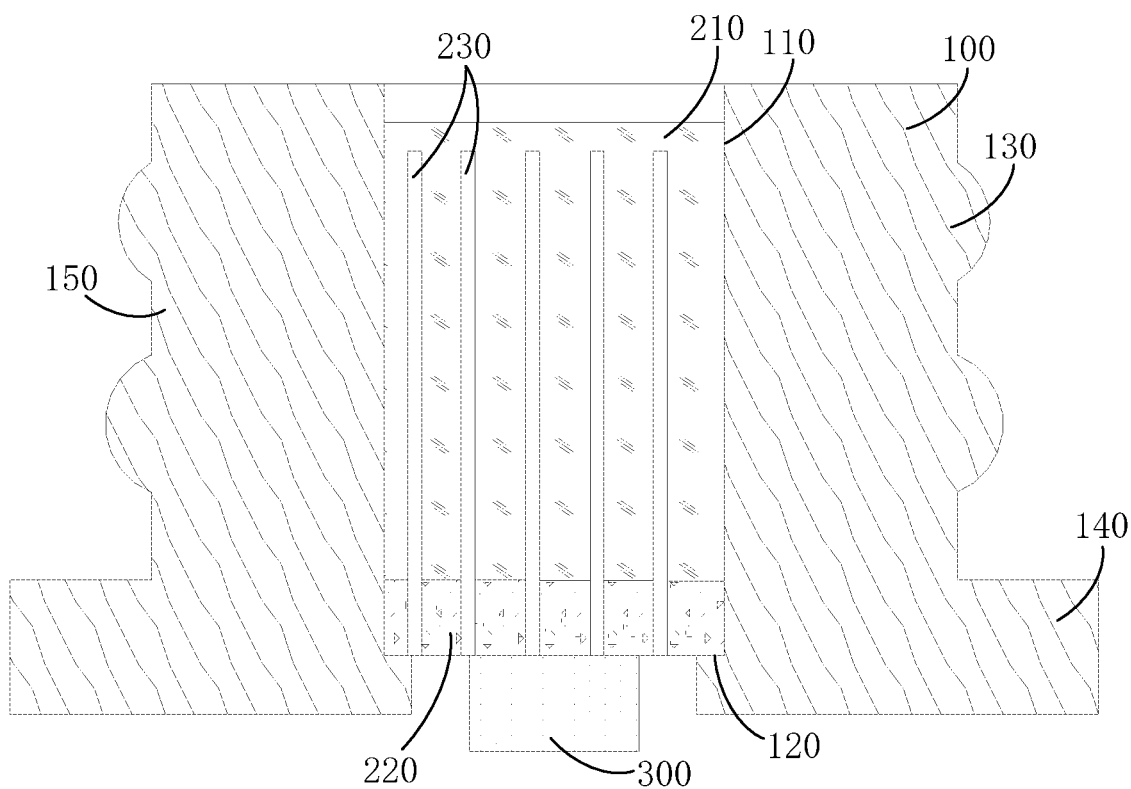
FIG. 7 is a cross-sectional view of a ventilation valve according to yet another embodiment.

Referring to FIG. 7, in an alternative embodiment, the oleophobic material layer 210 may be provided with a plurality of air inlet channels 230. The air inlet channel 230 may not penetrate an end surface of the oleophobic material layer 210 adjacent to the storage cavity 21. That is, there is a preset distance from a top end of the air inlet channel 230 to the end surface of the oleophobic material layer 210, so as to prevent the liquid from entering the air inlet channel 230, thus ensuring the liquid isolation property of the oleophobic material layer 210. A diameter of the air inlet channel 230 may be greater than the diameter of the air-permeable micropore of the oleophobic material layer 210. For example, the diameter of each air inlet channel 230 may range from about 0.5 mm to about 1.5 mm, which may specifically be 0.5 mm, 0.7 mm, 0.8 mm, 1.5 mm or the like. Through the provision of the air inlet channel 230, a large amount of air can flow into the air inlet channel 230 first, and then enter the air-permeable micropores from the air inlet channel 230 to quickly diffuse into the storage cavity 21. Therefore, the air inlet channel 230 can significantly increase the speed of the air entering the storage cavity 21, ensuring that the storage cavity 21 can be quickly replenished with air and the air pressure therein is timely kept within the normal range. Central axes of the air inlet channels 230 may also be parallel with a central axis of the through hole 110, such that the air can enter the storage cavity 21 through the shortest diffusion path, which further increases the speed of the air entering the storage cavity 21. The air inlet channel 230 extends from an end away from the storage cavity 21 in a direction towards the storage cavity 21 but does not communicate with the storage cavity 21. The depth of the air inlet channel 230 may be greater than 50% but less than 80% of the thickness of the oleophobic material layer 210, thus ensuring better air permeability and higher mechanical strength of the oleophobic material layer 210.

In one embodiment, the air inlet channel 230 in the oleophobic material layer 210 may further extend into the semi-permeable membrane 220. For example, there is a preset distance from an end of the air inlet channel 230 to the end surface of the oleophobic material layer 210, while the other end of the air inlet channel 230 may extend through the entire semi-permeable membrane 220, such that the air permeability of the valve element 200 can be further improved while ensuring the liquid isolation property.

Each the technical features of the embodiments described above can be arbitrarily combined. In order to simplify the description, all possible combinations of each technical features in the above embodiments have not been described. However, as long as there is no contradiction in the combination of these technical features, it should be considered as that all of them fall within the scope recorded in this specification.

The above described embodiments only present several implementation manners of the present disclosure, and descriptions thereof are more specific and detailed, but they cannot be understood as limiting the scope of the application patent. It should be noted that, to those of ordinary skill in the art, several modifications and improvements can be made without departing from the concept of the present disclosure, which all fall within the protection scope of the present disclosure. Therefore, the protection scope of this application patent shall be subject to the appended claims.

What is claimed is:

1. A ventilation valve configured to be mounted to a liquid reservoir of an electronic atomizing device, the ventilation valve comprising:
    a valve sleeve connected to the liquid reservoir and provided with a through hole in communication with a storage cavity of the liquid reservoir; and
    a valve element having air permeability and comprising an oleophobic material layer adjacent to the storage cavity, and a semi-permeable membrane connected to an end of the oleophobic material layer away from the storage cavity, the oleophobic material layer being accommodated in the through hole.

2. The ventilation valve according to claim 1, wherein the oleophobic material layer includes a rigid oleophobic material layer.

3. The ventilation valve according to claim 1, wherein in an axial direction of the through hole, a thickness of the oleophobic material layer is greater than a thickness of the semi-permeable membrane.

4. The ventilation valve according to claim 3, wherein the thickness of the oleophobic material layer is in a range from about 0.5 mm to about 2 mm, and the thickness of the semi-permeable membrane is in a range from about 10 μm to about 50 μm.

5. The ventilation valve according to claim 1, wherein a stepped portion is formed on an inner surface of the through hole, an end of the valve element abuts against the stepped portion.

6. The ventilation valve according to claim 1, wherein the semi-permeable membrane is accommodated in the through hole.

7. The ventilation valve according to claim 1, wherein an end of the valve element adjacent to the storage cavity is lower than a top portion of the valve sleeve by a preset height difference.

8. The ventilation valve according to claim 1, wherein the valve element is provided with a plurality of air inlet channels, a diameter of each air inlet channel ranges from about 0.5 mm to about 1.5 mm.

9. The ventilation valve according to claim 8, wherein central axes of the air inlet channels are parallel with a central axis of the through hole.

10. The ventilation valve according to claim 8, wherein there is a preset distance from one end of the air inlet channel to an end surface of the valve element adjacent to the storage cavity, the other end of the air inlet channel extends through an end surface of the valve element away from the storage cavity.

11. The ventilation valve according to claim 1, further comprising dust filter provided at an end surface of the valve element away from the storage cavity.

12. The ventilation valve according to claim 11, wherein the dust filter is integrally formed with the semi-permeable membrane; the valve sleeve is made of silicone.

13. A ventilation valve configured to be mounted to a liquid reservoir of an electronic atomizing device, the ventilation valve comprising:
    a valve sleeve connected to the liquid reservoir and provided with a through hole in communication with a storage cavity of the liquid reservoir; and
    a valve element having air permeability and comprising an oleophobic material layer adjacent to the storage cavity, and a semi-permeable membrane connected to an end of the oleophobic material layer away from the storage cavity, the oleophobic material layer filling at least a part of the through hole;
    wherein the valve sleeve comprises a main body fixed in the liquid reservoir and a flange portion connected to an end of the main body away from the storage cavity, the flange portion being configured to abut against the liquid reservoir.

14. The ventilation valve according to claim 1, further comprising a plurality of protruding rings provided on an outer surface of the valve sleeve, the plurality of protruding rings are spaced apart with an interval in an axial direction of the valve sleeve, the plurality of protruding rings are configured to be embedded in the liquid reservoir.

15. A ventilation valve configured to be mounted to a liquid reservoir of an electronic atomizing device, the ventilation valve comprising:
    a valve sleeve connected to the liquid reservoir and provided with a through hole in communication with a storage cavity of the liquid reservoir; and
    a valve element having air permeability and comprising an oleophobic material layer adjacent to the storage cavity, and a semi-permeable membrane connected to an end of the oleophobic material layer away from the storage cavity, the oleophobic material layer filling at least a part of the through hole;
    wherein the valve element comprises a plurality of oleophobic material layers and a plurality of semi-permeable membranes that are alternately arranged in an axial direction of the through hole.

16. The ventilation valve according to claim 15, wherein each of the plurality of semi-permeable membranes is connected to an end surface of the respective oleophobic material layer away from the storage cavity.

17. An electronic atomizing device, comprising:
    a liquid reservoir having a storage cavity; and
    the ventilation valve according to claim 1.

18. The electronic atomizing device according to claim 17, wherein the liquid reservoir is provided with a mounting hole communicating with the storage cavity, the ventilation valve is received in the mounting hole.

19. The electronic atomizing device according to claim 17, wherein an end of the valve element adjacent to the storage cavity is lower than a top portion of the valve sleeve by a preset height difference.

* * * * *